United States Patent [19]
Fischell et al.

[11] Patent Number: 5,879,282
[45] Date of Patent: *Mar. 9, 1999

[54] CATHETER HAVING AN EXPANDABLE RADIOACTIVE SOURCE

[75] Inventors: Robert E. Fischell, Dayton, Md.;
David R. Fischell, Fair Haven, N.J.;
Tim A. Fischell, Richland, Mich.

[73] Assignee: Cordis a Johnson and Johnson Company, Miami Lakes, Fla.

[ * ] Notice: The term of this patent shall not extend beyond the expiration date of Pat. No. 5,730,698.

[21] Appl. No.: 786,677

[22] Filed: Jan. 21, 1997

[51] Int. Cl.⁶ .................................................. A61N 5/00
[52] U.S. Cl. ............................................................. 600/3
[58] Field of Search ........................................... 600/1–8

[56] References Cited

U.S. PATENT DOCUMENTS

| | | |
|---|---|---|
| 5,302,168 | 4/1994 | Hess .................................. 600/3 |
| 5,411,466 | 5/1995 | Hess .................................. 600/3 |
| 5,484,384 | 1/1996 | Fearnot ............................. 600/3 |
| 5,730,698 | 3/1998 | Fischell et al. ..................... 600/3 |

FOREIGN PATENT DOCUMENTS

| | | | |
|---|---|---|---|
| 0497495 | 5/1992 | European Pat. Off. | ......... A61N 5/10 |
| 793158 | 4/1958 | United Kingdom . | |

*Primary Examiner*—John P. Lacyk

[57] ABSTRACT

A balloon catheter for irradiation with or without dilatation of an arterial stenosis has an inflatable balloon and a generally cylindrical, thin-walled, elastic radioactive source both located coaxially at a distal section of the balloon catheter. The elastic radioactive source is moved radially outward as a result of injection of an inflation fluid into the inflatable balloon thus placing the radioactive source in close proximity to the wall of a vessel of the human body into which the balloon catheter has been inserted.

30 Claims, 9 Drawing Sheets

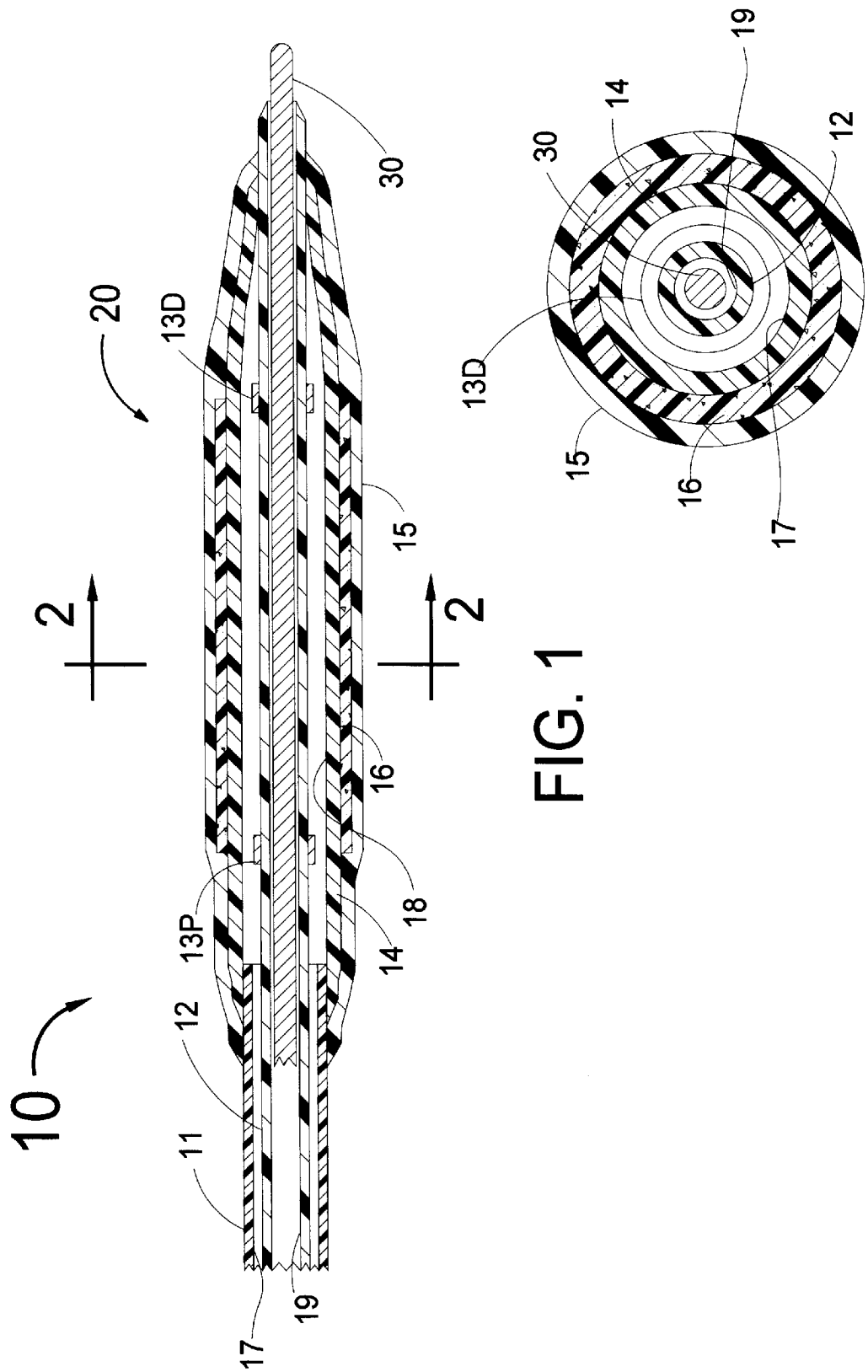

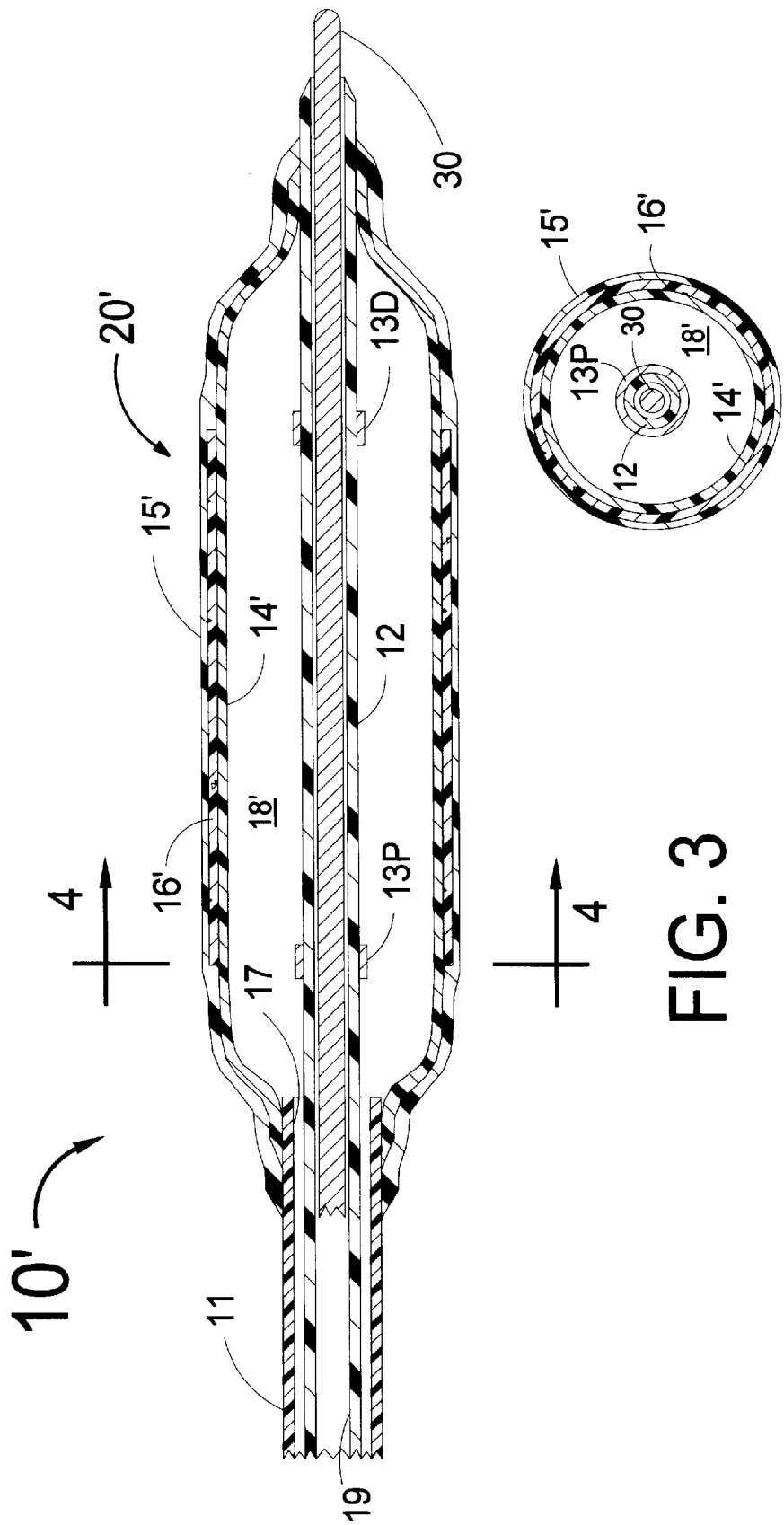

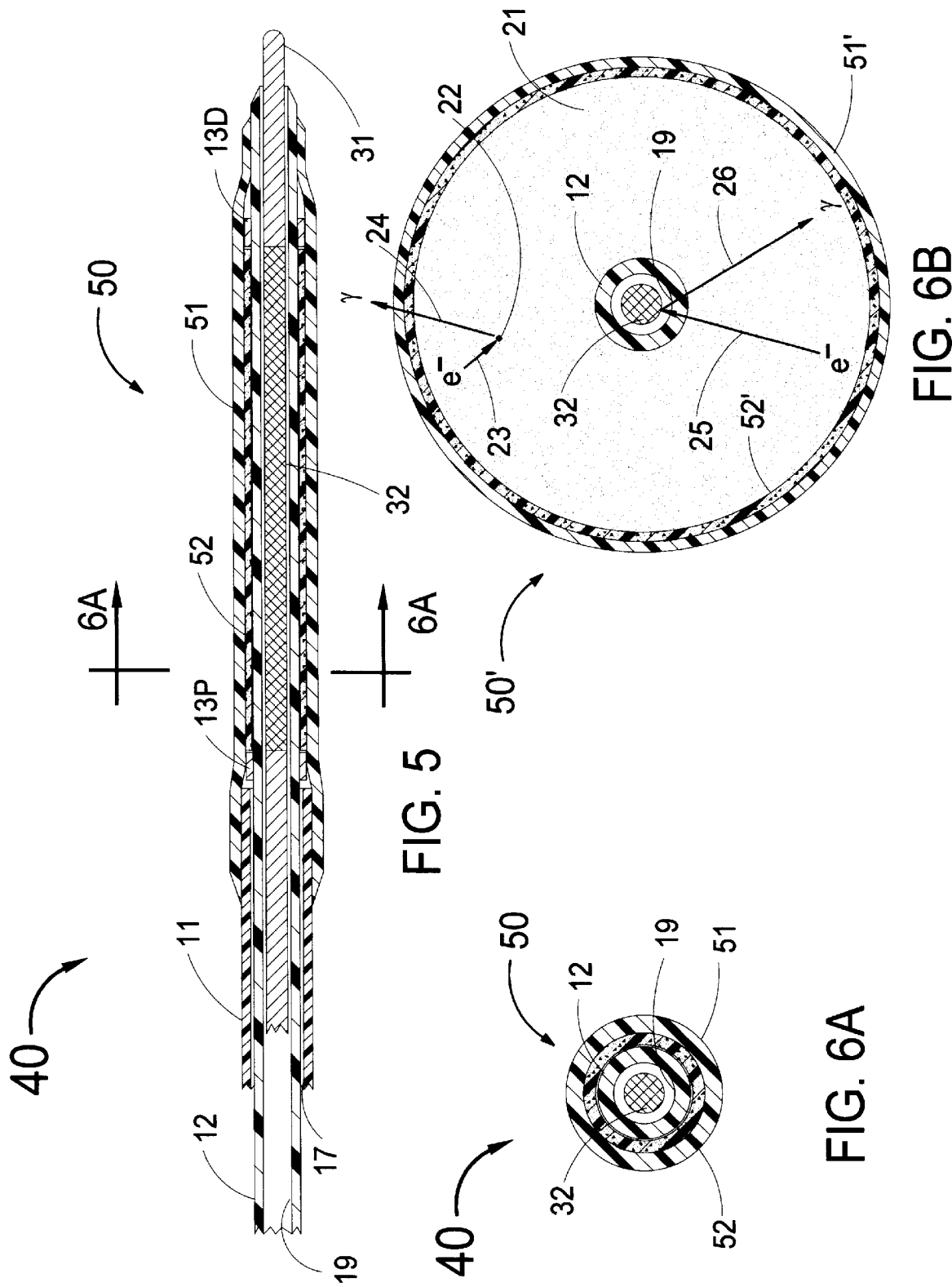

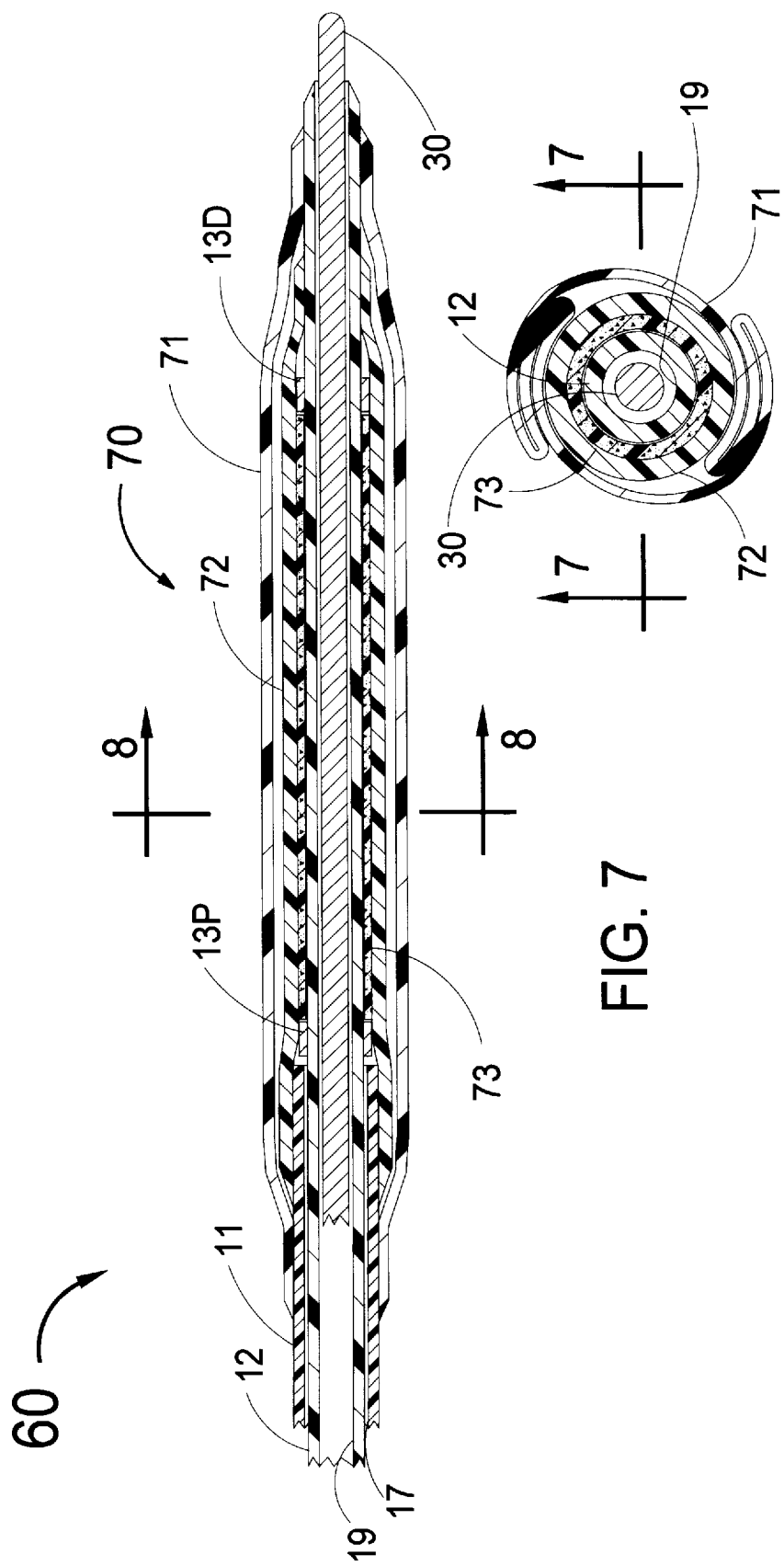

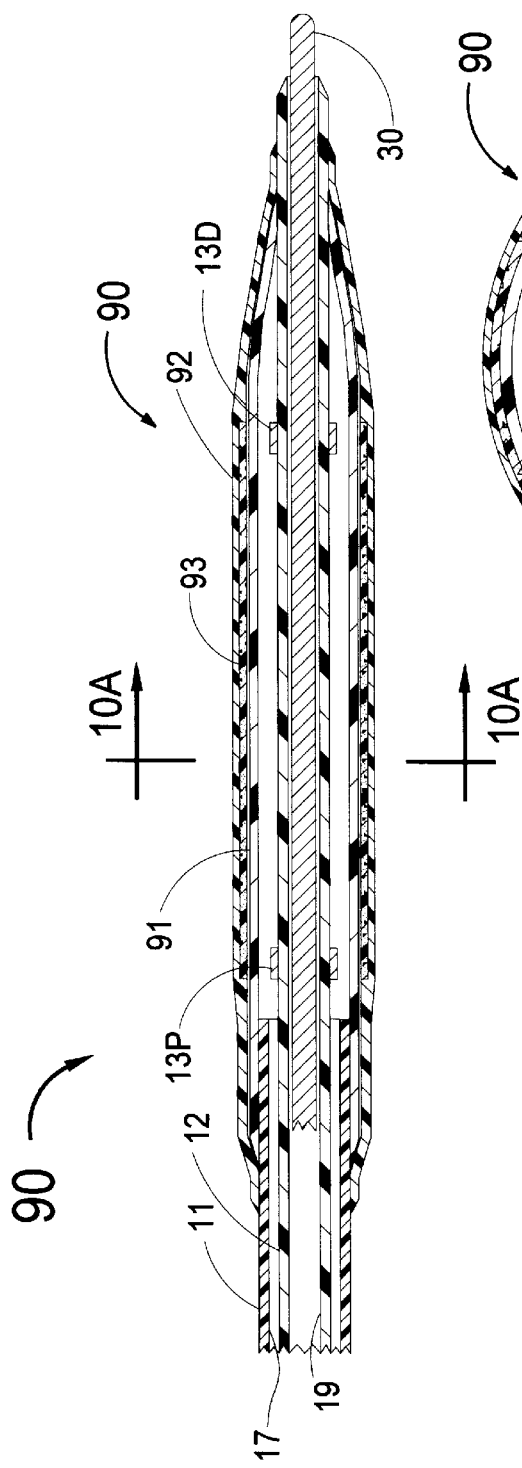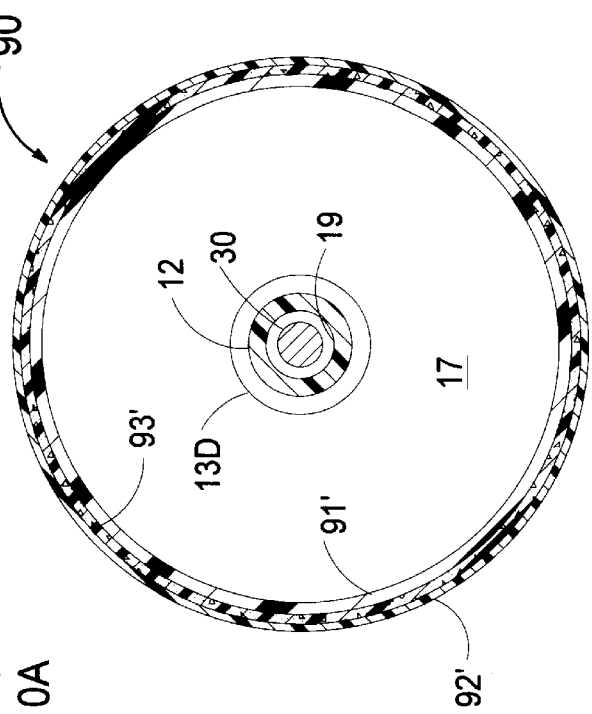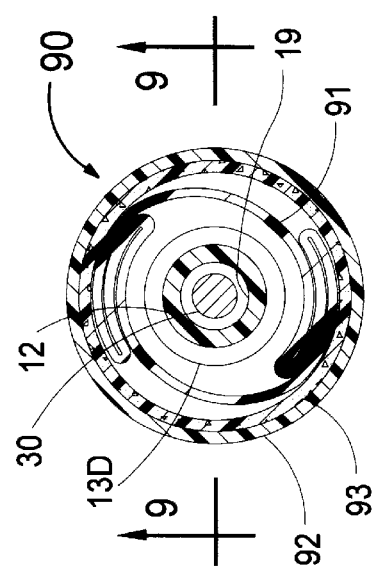

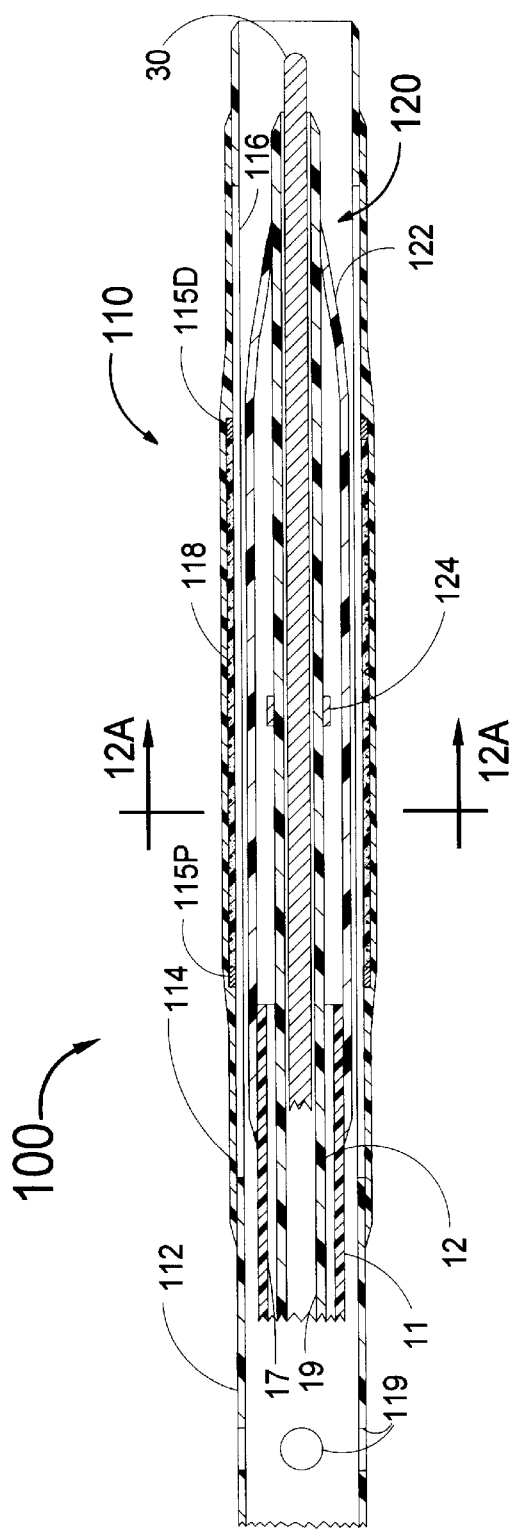
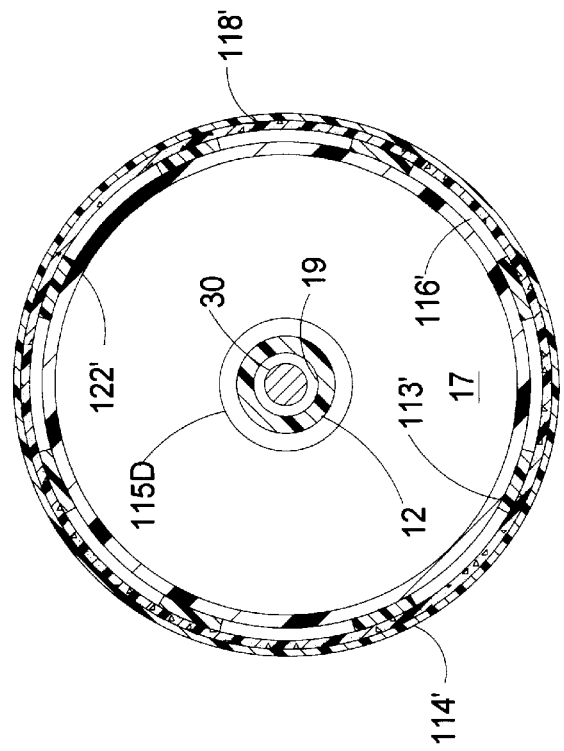
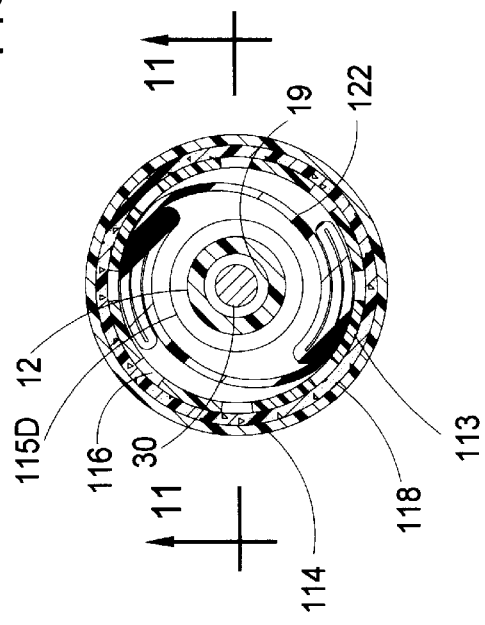
FIG. 11
FIG. 12A
FIG. 12B

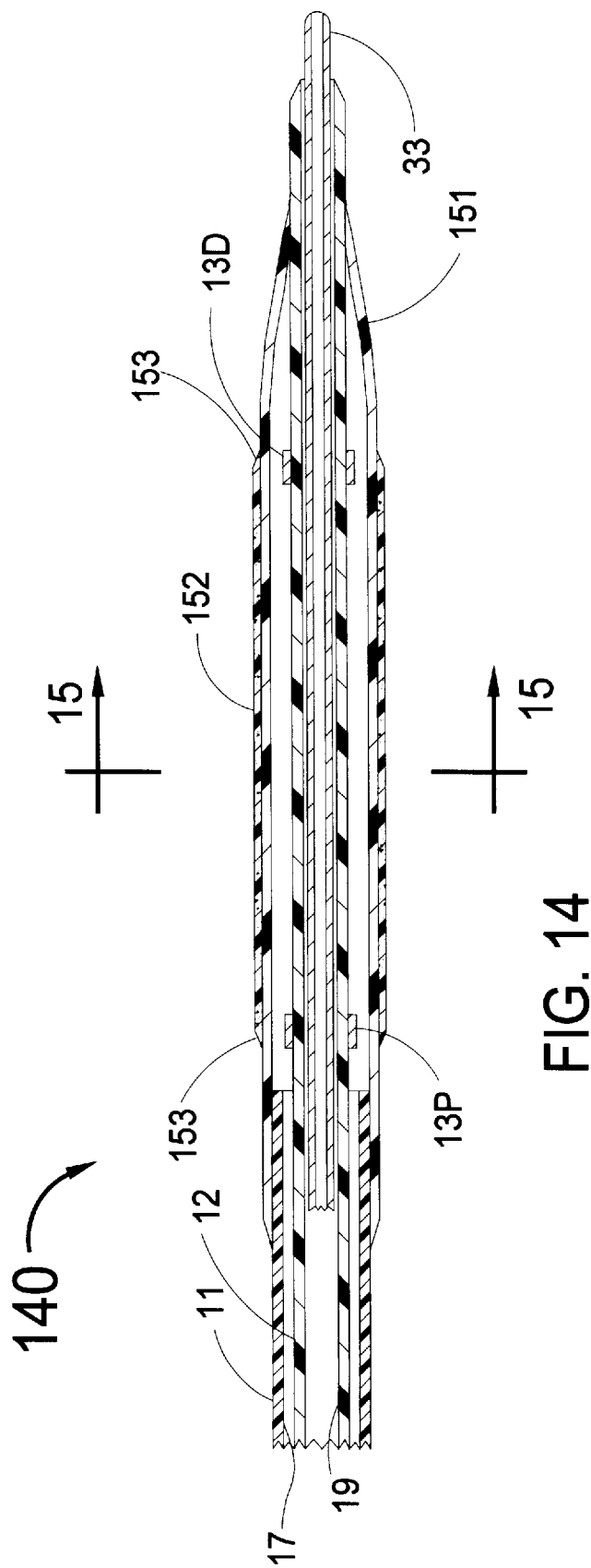
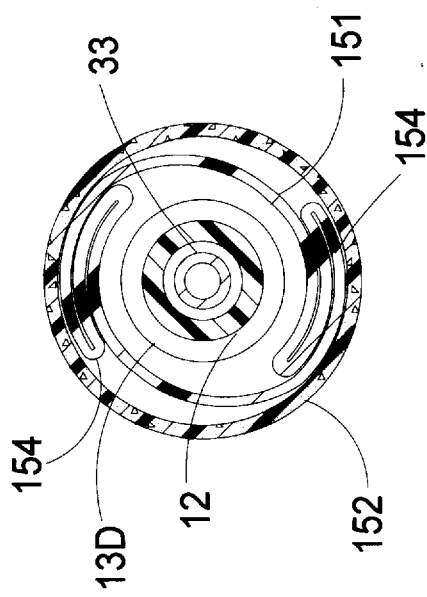
FIG. 14
FIG. 15

CATHETER HAVING AN EXPANDABLE RADIOACTIVE SOURCE

FIELD OF USE

This invention is in the field of intravascular catheters that apply radiation to the wall of a blood vessel to decrease the rate of restenosis after angioplasty, atherectomy or stent implantation.

BACKGROUND OF THE INVENTION

In U.S. Pat. No. 5,411,466, R. L. Hess discloses a balloon angioplasty catheter having "an angioplasty balloon with dose means in the form of radioactive elements attached thereto." In U.S. Pat. No. 5,484,384, N. E. Fearnot discloses a balloon filled with a radioactive fluid that "is injected into the balloon for irradiating the treatment site."

One problem with the Hess invention is that separate radioactive elements on the outside of an angioplasty balloon can become detached, particularly when the balloon expands, which can result in distal emboli that can block a downstream artery. Also patches on the balloon's exterior surface could leach out radioactive matter into the blood stream which is undesirable. Still further, patches on the balloon's exterior surface do not provide uniform irradiation of the tissue of the arterial wall which again is undesirable.

Placing a radioactive liquid into a balloon is highly undesirable because the balloon angioplasty catheter can leak or break and release the radioactive fluid into the blood stream. Furthermore, a radioactive fluid leak can occur where the fluid is injected at the proximal end of the balloon catheter.

SUMMARY OF THE INVENTION

The invention disclosed herein overcomes the shortcomings of prior art radioactive sources for the prevention of vascular restenosis. Specifically, one embodiment of this invention is a radioactive source in the general form of an elastic cylinder placed between highly compliant, elastic, inflatable balloons. The advantages of this design over the prior art radiation dosing means are as follows:

(1) Since an elastic balloon at the distal end of a catheter can be expanded from a 1.0 mm initial diameter to a 20.0 mm inflated diameter, one size balloon can fit essentially all diameters of blood vessels that require treatment.

(2) Since the radioisotope is not in a liquid form, there is nothing that could leak.

(3) Since there is an elastomer balloon wall on each side of the radioactive material, there is no chance of leaching out of the radioactive material into the blood stream.

(4) Since the balloon material and the radioactive source are highly compliant, they will make contact with the arterial wall even if the dilated stenosis has an irregular interior surface, thus providing more uniform dosing to the injured tissue of the wall of the blood vessel.

(5) Since the radioactive source is preferably in the general form of a cylinder, it provides a more precise and uniform dosing of the dilated blood vessel as compared to having the dosing means in the form of patches on the balloon's exterior surface.

(6) Since the radioactive source is interior to the elastic balloon, there is no chance that the radioactive source will break off and obstruct a downstream blood vessel.

Another embodiment of this invention is an elastic balloon catheter that has a radioactive source in the form of a radioisotope placed into an elastomer and then formed into a cylinder that is placed inside the elastic balloon. This embodiment has essentially all the same advantages as listed in items (1) through (6) above. Although this design allows contact between the liquid used to inflate the elastic balloon and the radioisotope source, so little would leach out during a 1.0 to 10.0 minute inflation as to not be a hazard for disposal of the inflation liquid. More importantly, no radioisotope would leach out into the patient's tissue or bloodstream.

Still another embodiment of this invention combines an angioplasty balloon with an elastic balloon that has a separate elastic radioactive cylinder that is attached to the elastic balloon. The elastic balloon can lie either inside or outside the angioplasty balloon, but in no case does the radioactive source make direct contact with the vessel wall. An advantage of a design combining an angioplasty balloon with a cylindrical elastic radioactive source is that the angioplasty balloon, being a non-compliant, high pressure balloon, that goes to a fixed diameter somewhat simplifies the calculation of the radiation dose to the tissue of the vessel wall.

Still another embodiment of this invention is a catheter in the form of an elongated sheath having an elastic tube at its distal end. The elastic tube includes an elastic cylinder into which has been placed a radioactive material. The elastic cylinder can be expanded against the wall of an artery by expanding the balloon of a balloon angioplasty catheter which balloon is first placed within the elastic tube.

Still another embodiment of this invention is either an elastic balloon or an angioplasty balloon in which a radioisotope is placed within the elastomer of an elastic balloon or the plastic material that forms an angioplasty balloon. This design has the advantage of simplicity even though some radioactive material could leach out into the blood stream or into the fluid that is used to inflate the balloon.

All the embodiments described above have the advantage of placing the radioactive source in an optimum position; i.e., in close proximity to the arterial wall. This is a more efficient use of the radioisotope source material as compared to either the use of a radioactive liquid to fill a angioplasty balloon or the placement of the radioisotope at the tip of a wire-like catheter that is much smaller in diameter as compared to the artery into which the catheter tip is placed. By more efficient is meant that by using an expandable radioisotope source, one can get the same radiation dose to the arterial wall with fewer milliCuries (mCi) of radioactive material.

Thus, the most important object of this invention is to provide a means to uniformly and efficiently irradiate an arterial wall by placing an expandable, generally cylindrical radioisotope source in close proximity to that arterial wall.

Another object of this invention is to have a radioactive source that is highly elastic.

Still another object of this invention is to have a radioactive source wherein one size fits a large range of blood vessel diameters.

Still another object of this invention is to have the outside of an elastic balloon containing a radioactive source make a consistent contact with the interior wall surface of a dilated blood vessel even if that surface is highly irregular as to roundness and/or diameter.

Still another object of this invention is to have a highly elastic radioactive source in the general form of a cylinder so that dosing of the damaged tissue of the blood vessel wall can be calculated more accurately.

Still another object of this invention is to have a highly elastic radioactive source in the general form of a cylinder so that dosing of the damaged tissue of the blood vessel wall is more uniformly applied as compared to a wire tip as a source of radiation or compared to separate patches of radioactive material placed on the exterior surface of an inflatable angioplasty balloon.

Still another object of this invention is to have a radioactive source on a catheter in a form that prevents radioactive material from breaking off into the blood stream when the balloon expands or should the balloon burst.

Still another object of this invention is to have a radioactive source that can accurately irradiate a long dilated stenosis by successively advancing the radioactive source in a longitudinal direction using two radiopaque marker bands as indicators of the longitudinal position of the radioactive source.

Still another object of this invention is to have a radioactive source that will not leach material into the blood stream or into the fluid used to fill the balloon.

Still another object of this invention is to inject into the balloon catheter an inflation liquid to expand an elastic radioactive source which liquid has an increased concentration of radiopaque contrast medium so as to increase gamma ray bremstrahlung during the time of irradiation. Still another object of this invention is to use an inflation liquid that includes dissolved or particulate matter having a high atomic number so as to enhance gamma ray bremsstrahlung so as to enhance the irradiation of a thick-walled vessel.

Still another object of this invention is to use a guide wire having a distal section made from a metal having a high atomic number so as to enhance gamma ray bremsstrahlung so as to enhance the irradiation of a thick-walled vessel.

Still another object of this invention is to use a guide wire having one or two distal sections made from a high density metal which distal section is highly radiopaque and which can be placed to mark the site of a dilated stenosis in order to expeditiously position a radioactive source at that location.

Still another object of this invention is to use an elastic, beta particle emitting, radioactive source to prevent irradiation of the health care staff who are treating the patient because beta particles have a very short range and sources of beta radiation can be easily shielded.

Still another object of this invention is to place a radioisotope source directly into the material from which an elastic balloon or an angioplasty balloon is made.

Still another object of this invention is to have a radioactive material placed in an elastic cylinder that is expandable by the balloon of a balloon catheter so as to place the radioactive material in close proximity to but not in contact with the arterial wall.

Still another object of this invention is a method to pre-dilate an arterial stenosis prior to stenting while simultaneously irradiating the dilated tissue.

These and other important objects and advantages of this invention will become apparent from the detailed description of the invention and the associated drawings provided herein.

BRIEF DESCRIPTION OF THE DRAWINGS

FIG. 1 is a longitudinal cross section of a distal section of an elastic balloon catheter showing an elastic radioactive source placed between two uninflated elastic balloons.

FIG. 2 is an enlarged transverse cross section of the distal section of the uninflated balloon assembly at section 2—2 of FIG. 1.

FIG. 3 is a longitudinal cross section of the distal section of the balloon catheter showing the elastic radioactive source and the two elastic balloons in the inflated state.

FIG. 4 is a transverse cross section of the inflated balloon at section 4—4 of FIG. 3.

FIG. 5 is a longitudinal cross section of a distal section of an elastic balloon catheter showing an elastic balloon into which is placed an elastic cylinder which is a radioactive source.

FIG. 6A is an enlarged transverse cross section of the elastic balloon and elastic radioactive cylinder at section 6A—6A of FIG. 5.

FIG. 6B is an enlarged transverse cross section of the elastic balloon of FIGS. 5 and 6A shown in its inflated state.

FIG. 7 is a longitudinal cross section of a distal section of a two balloon catheter system having an external angioplasty balloon and a separate internal elastic balloon to which a cylindrical elastic radioactive source has been attached.

FIG. 8 is an enlarged transverse cross section of the two balloon catheter system at section 8—8 of FIG. 7.

FIG. 9 is a longitudinal cross section of a distal section of a two balloon catheter system having an internal angioplasty balloon and a separate external elastic balloon to which a cylindrical elastic radioactive source has been attached.

FIG. 10A is an enlarged transverse cross section of the two balloon catheter system at section 10A—10A of FIG. 9.

FIG. 10B is an enlarged transverse cross section of the two balloon catheter system of FIGS. 9 and 10A with the balloon assembly shown in its inflated state.

FIG. 11 is a longitudinal cross section of a distal section of a conventional balloon angioplasty catheter having a surrounding sheath which has an elastic distal section that includes a radioactive source.

FIG. 12A is an enlarged transverse cross section of the catheter system of FIG. 11 at section 12A—12A.

FIG. 12B is an enlarged transverse cross section of the catheter system of FIGS. 11 and 12A shown with the angioplasty balloon in its inflated state.

FIG. 14 is a longitudinal cross section of a distal section of a conventional balloon angioplasty catheter that has a cylindrical elastic radioactive source placed around the angioplasty balloon.

FIG. 15 is an enlarged transverse cross section of the catheter system of FIG. 14 at section 15—15.

DETAILED DESCRIPTION OF THE INVENTION

Figure 13:
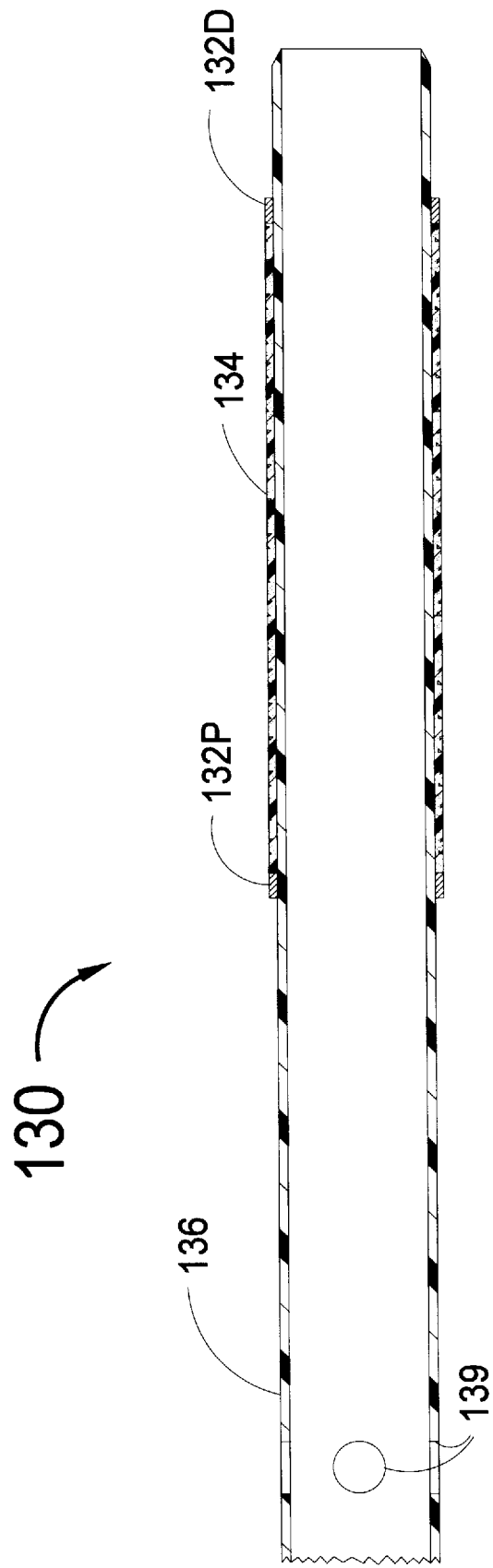
FIG. 13 is a longitudinal cross section of a distal section of an elastic sheath having a distal section that includes a radioactive source.

FIG. 1 shows a longitudinal cross section of a distal section of an elastic balloon catheter 10. The elastic balloon catheter 10 has a radioactive elastic balloon assembly 20, an outer shaft 11, inner shaft 12, proximal radiopaque marker band 13P and distal radiopaque marker band 13D and the guide wire lumen 19 through which a flexible guide wire 30 can be passed. The balloon assembly 20 consists of an inner elastic balloon 14, an outer elastic balloon 15 and an elastic cylindrical radioactive source 16. The proximal end of the inner elastic balloon 14 is adhesively joined to a distal section of the outer shaft 11, and a distal section of the balloon 14 is adhesively joined to a distal section of the inner shaft 12. The outer elastic balloon 15 is shrunk onto or adhesively joined to the inner balloon 14 and is also joined to the elastic radioactive source 16 which is in the form of an elastic cylinder that is placed between the inner balloon 14 and the outer balloon 15 as shown in FIGS. 1 and 2. This radioactive source 16 could be merely placed between the balloons 14 and 15 or it could be adhesively joined to either one or both of the balloons 14 and 15. FIG. 1 also shows the annular passageway 17 which is in fluid communication with the balloon inflation chamber 18. FIG. 2 also shows a transverse cross section of the inner shaft 12, the distal radiopaque marker band 13D, the guide wire lumen 19 and the guide wire 30.

FIG. 3 shows the distal section of the elastic balloon catheter 10' having inflated balloons 14' and 15' and the expanded elastic radioactive source 16' which all together form the inflated radioactive elastic balloon assembly 20'. FIG. 3 also shows the outer shaft 11, the inner shaft 12, the proximal radiopaque marker band 13P, the distal radiopaque marker band 13D, the guide wire lumen 19 and the guide wire 30. An inflation liquid which is typically a radiopaque contrast medium is injected at the proximal section of the annular passageway 17 (which lies outside the patient's body) which causes the inflation chamber 18' to be inflated. The guide wire lumen 19 can emerge proximally from the proximal end of the elastic balloon catheter 10 (or 10') which is the well known "over-the-wire" type of catheter, or the proximal section of the guide wire lumen 19 could emerge just proximal to the proximal end of the balloon assembly 20' which is the well known "rapid exchange" type of catheter.

It should be noted that, unlike an angioplasty balloon which is inelastic and doesn't change its balloon wall thickness upon expansion, the elastic balloon assembly 20' consisting of the inner balloon 14', outer balloon 15' and elastic radioactive source 16' all decrease in wall thickness when the chamber 18' is filled with contrast medium. Thus, the source intensity per square centimeter of surface of the elastic radioactive source 16' varies with the diameter of the chamber 18'.

Unlike angioplasty balloons which typically require at least 6 atmospheres for an inflation pressure, the balloon assembly 20' of the elastic balloon catheter 10' should be able to be inflated to any diameter up to and including 20 mm at a fluid pressure of less than 5 atmospheres and preferably less than 3 atmospheres.

As the elastic balloon assembly 20' is inflated, the radioactive source 16' is placed in near contact (except for the wall thickness of the outer balloon 15') with a previously dilated blood vessel. Thus, even though the dilated stenosis in an artery is somewhat irregular in shape, the source 15' will, because of its elasticity, conform to that shape. This highly desirable attribute provides a more uniform radiation dose to the arterial wall. This balloon conformance to the vessel wall will also be true if a stent has been previously placed at the site of a dilated stenosis.

It should be pointed out that the invention illustrated in FIGS. 1 to 4 inclusive is not a balloon angioplasty catheter and does not utilize an angioplasty balloon. The balloon assembly 20 because it is highly elastic and expandable to very large diameters at comparatively low pressures is not an angioplasty balloon. All angioplasty balloons go to a more-or-less fixed diameter which is the "nominal" diameter of the angioplasty balloon. Also, angioplasty balloons are dramatically less compliant compared to elastic balloons and operate at pressures of 6 to 16 atmospheres. The design of FIGS. 1 to 4 inclusive would not be effective in dilating an arterial stenosis.

It should also be understood that a radioactive material could be placed into the material of the balloon 14 or the balloon 15 and the cylindrical elastic radioactive source 16 could be eliminated. All other features of this catheter with an elastic balloon would otherwise remain the same as that shown in FIGS. 1 to 4 inclusive. Although this could provide direct contact between the radioisotope and the arterial wall and blood and also the fluid used to fill the balloon 14, it would be a simpler design which may be easier and less expensive to make. By placing the radioactive material only into the elastic balloon 14, there would be no exposure of the blood to the radioactive material.

A second embodiment of the present invention which includes an elastic balloon is shown in FIGS. 5, 6A and 6B. FIGS. 5, 6A and 6B show the same type of catheter construction as shown in FIGS. 1 to 4 inclusive, namely an outer shaft 11, inner shaft 12, radiopaque marker bands 13P and 13D, an annular fluid passageway 17 that is used to inflate and deflate the balloon assembly 50, a guide wire lumen 19 and a guide wire 31 having a highly radiopaque distal portion 32. FIGS. 5 and 6A also show an elastic balloon catheter 40 having a uninflated balloon assembly 50 consisting of an elastic balloon 51 to which is attached a cylindrical elastic radioactive source 52. The radioactive source 52 could be placed on either the interior surface of the elastic balloon 51 as shown in FIGS. 5, 6A and 6B or it could be placed on the exterior surface of the balloon 51. It should also be noted that the radioactive source 52 and elastic balloon 51 would both change wall thickness as they expand which is clearly shown in the transverse cross section of the inflated balloon assembly 50' consisting of the expanded elastic balloon 51' and the expanded radioactive source 52' as shown in FIG. 6B. It should also be noted that by placing the radioactive source 52 between the radiopaque marker bands 13P and 13D, the distal profile of the elastic balloon catheter 40 is minimized which is a highly desirable attribute for such a catheter.

The method for using this invention would typically be as follows:

(a) Pre-dilate an arterial stenosis with an appropriately sized balloon angioplasty catheter.

(b) If desired, place a stent at the site of the dilated stenosis.

(c) Remove the balloon catheter (and/or the stent delivery catheter) and advance the elastic balloon catheter 10 or 40 over a conventional guide wire 30 or a guide wire 31 having a highly radiopaque distal portion that has been placed through the dilated stenosis. An inflation fluid which is a gas such as carbon dioxide could also be used.

(d) Inject an inflation fluid such as liquid contrast medium into the proximal section of the annular passageway 17 so as to inflate the balloon assembly 20' or 50' so that the radioactive source 16' or 52' is moved radially outward against the arterial wall at the site of the dilated arterial stenosis. An inflation fluid carbon dioxide could also be used.

(e) Expose the dilated stenosis for a sufficient time to obtain an arterial wall dose that is greater than 500 centiGrey (cGy).

(f) If the patient develops chest pain during the inflation time, then deflate the balloon assembly 20' or 50' for 10 to 30 seconds and then re-inflate the balloon assembly 20' or 50' for a second period of time.

(g) Repeat step (f) as many times as necessary to obtain the desired dose to the arterial wall.

(h) Deflate the balloon assembly 20' or 50' and remove the elastic balloon catheter 10' or 40' from the patient's body.

It may be highly desirable to increase gamma ray emission to irradiate a human vessel having a thicker wall by increasing the concentration of the contrast medium used for balloon inflation to a "higher concentration". Typically, contrast medium for balloon inflation is a 50 percent iodine solution in normal saline. Anything greater that 55 percent iodine solution would be considered a "higher concentration" of contrast medium. Gamma-rays or x-rays resulting from bremsstrahlung from a beta particle emitting radioactive source could be further enhanced by placing particles or dissolved matter from a high atomic number material into the liquid used to inflate the balloon assembly 20' or 50'. This is best seen in FIG. 6B which has an inflation liquid 21 that includes a solute or particles 22 of a high atomic number material being hit by an electron (e) traveling along the path 23. A "high atomic number" material can be defined as having an atomic number greater than 53. As a result of bremsstrahlung, the electron when colliding with a high atomic number atom would emit a gamma-(or x-) ray along the path 24. This method of using a highly concentrated contrast medium or another material having a high atomic number would improve the efficiency for irradiating arterial wall tissue and would particularly enhance the dose and dose rate of the more distant arterial wall tissue such as the adventitia. A lead apron could be placed over the patient during balloon inflation or a leaded glass radiation protection screen could be used to decrease radiation exposure of the health care workers. It should be noted that such a liquid that includes a high atomic number solute or particle would become a gamma-ray and/or x-ray emitter only in the presence of the beta particle emitting radioactive source. If such a liquid would escape from a ruptured balloon, it would not be radioactive and therefore would not adversely affect the patient. When the balloon is deflated, the liquid that is removed would not be radioactive so that there would be no problem with leakage as there would if a radioactive liquid were used.

Another method to increase x-ray and gamma-ray emission from a beta-particle emitting balloon, would be to place a specially made guide wire 31 into the guide wire lumen 19. Such a special guide wire would have a distal portion 32 made from a high density metal (such as tantalum) which would use bremsstrahlung from the beta-particles emitted from an inflatable radioactive source to cause increased x-ray and gamma-ray radiation of the patient's arterial wall. A high density metal is defined herein as having a specific gravity greater than 9.0. FIG. 6B shows a beta particle moving along the path 25 hitting the guide wire section made from a high density metal which causes a gamma-ray (or x-ray) to be emitted along the path 26. Because a high density metal such as tantalum is also highly radiopaque, the distal portion 32 can also be advantageously used to mark a site of a dilated stenosis or a stent so that the balloon assembly 50 can be expeditiously advanced to that exact site.

Ideally, the elastic radioactive source 16 or 52 would be formed by dispersing a beta particle emitting isotope such as phosphorous 32 (P-32) into a highly elastic elastomer such as a low durometer silicone rubber. Other isotopes which could be used are strontium-90, yttrium-90 or any other isotope which is predominantly a beta particle emitter. Ideally the P-32 would be in the form of a stable molecule in which the P-32 is covalently bonded for example orthophosphate, sodium phosphate or adenosine triphosphate (ATP). Because ATP is a large molecule that will not tend to leach out, it is a particularly appropriate compound to use where the plastic or elastic material that contains the radioisotope source makes contact with the blood and arterial wall. It may also be desired to incorporate a gamma or a combined gamma plus beta radioisotope material into the plastic or elastic material from which the radioactive source is made.

A third and fourth embodiment of the present invention, which embodiments include an angioplasty balloon, are shown in FIGS. 7, 8, 9, 10A and 10B. These inventions have the capability to both dilate a stenosis and apply radiation at the same time in order to prevent restenosis.

FIGS. 7 to 10B inclusive show the same type of catheter construction as shown in FIGS. 1 and 2, namely an outer shaft 11, inner shaft 12, radiopaque marker bands 13P and 13D, an annular fluid passageway 17 that is used to inflate and deflate the balloon assembly 70 or the balloon assembly 90, a guide wire 30 and a guide wire lumen 19.

FIGS. 7 and 8 show an angioplasty catheter system 60 having a balloon assembly 70 consisting of an angioplasty balloon 71 that is placed outside of an elastic balloon 72 to which is attached a cylindrical elastic radioactive source 73. The radioactive source 73 could be placed either inside the angioplasty balloon 71 as shown in FIGS. 7 and 8 or it could be placed on the outside of the angioplasty balloon 91 as shown in FIGS. 9, 10 and 10B. It should be noted that by placing the radioactive source 73 between the radiopaque marker bands 13P and 13D, the distal profile of the balloon angioplasty catheter 60 is minimized which is a highly desirable attribute for such a catheter. Also, the angioplasty balloon 71 expands to a predetermined nominal diameter essentially irrespective of the pressure to which it is inflated whereas the elastic balloon, if not restrained by the angioplasty balloon 71 would continue to expand to successively larger diameters as the inflation pressure is increased.

FIGS. 9, 10A and 10B show another embodiment of the present invention namely a balloon angioplasty catheter system 80 having a balloon assembly 90 consisting of an angioplasty balloon 91 placed inside an elastic balloon 92 that has an elastic cylindrical radioactive source 93 attached inside the elastic balloon 92 but not attached to the angioplasty balloon 91. This embodiment acts much like the invention of FIGS. 7 and 8 in that the radioactive source is mounted onto an elastic balloon that is separate from an angioplasty balloon of a balloon angioplasty catheter. In both these embodiments, the elastic balloon with its elastic cylindrical radioactive source is separate from the angioplasty balloon which can be inflated to a high pressure to dilate an arterial stenosis.

Ideally, the invention shown in FIGS. 7 to 10B inclusive can be used to pre-dilate an arterial stenosis prior to the insertion of a stent. This is typically accomplished with a balloon catheter having an angioplasty balloon that has a diameter that is between 2.0 mm 3.0 mm. Thus, a single diameter (such as 2.5 mm) could be used for all balloons that are capable of both pre-dilation prior to stent implantation and irradiation of the stenosed site. Limiting the number of diameters for such a device would significantly decrease the problem of keeping catheters in inventory at a hospital when using a comparatively short half-life isotope such as P-32. If only two lengths of the radioactive cylinders 73 or 93 are used, for example, 20 mm or 30 mm long, then it would be practical to make pre-dilation balloon catheter systems 60 or 80 with only one nominal balloon angioplasty catheter diameter of 2.5 mm, with one isotope P-32, and in only two lengths; namely, 20 mm and 30 mm. Since P-32 has a half-life of only 14.3 days, it would probably have a shelf life that is of a comparable time period. Therefore, it is very important to limit the number of different diameters in which such a P-32, balloon angioplasty catheter system would be provided. This is also true for the elastic balloon catheter design of FIGS. 1 to 6B inclusive which also would be made in only one diameter and with only one, two or three lengths such as 2, 3 and/or 4 cm long.

Another method for treating stenoses longer than 2 mm with a cylindrical radioactive source that is only 2 mm long would be to treat a first (proximal) length of the stenosis, then advance the catheter until the proximal radiopaque marker band 13P is at the longitudinal position where the distal radiopaque marker band 13D was previously situated. The cylindrical radioactive source would then be used again at that new location to irradiate the distal section of the stenosis. This could be repeated again for another 2 cm to irradiate a 6 cm long stenosis. Thus, a single, 2 cm long cylindrical radioactive source could be used to irradiate a 2, 4 or 6 cm length of dilated artery. This could also be accomplished after as stent has been placed into the dilated artery. More advantageously, a 3 cm long cylindrical radioactive source should be used so that there is always some overlap of the radioactive source at both ends of a dilated stenosis or at both ends of a 2 cm long stent. This technique could also be used for irradiating any vessel of a human body such as a vein, bronchial tubes, fallopian tubes, billiary duct and carotid arteries as well as any coronary or peripheral artery.

It should be understood that P-32 is an ideal radioactive source for this purpose because it is a beta emitter that is easily shielded to protect the health care workers who have to place the balloon 60 or 80 within the patient's vascular system. Furthermore, the comparatively short half-life makes it easy to dispose of the radioactive sources after the patient has been treated.

FIGS. 11, 12A and 12B show a fifth embodiment of the present invention in which a sheath 110 having an elastically expandable distal section is placed over the angioplasty balloon 122 of a conventional balloon angioplasty catheter 120 to form another type of balloon angioplasty catheter system 100 that utilizes an elastic radioactive cylinder 118 for irradiating a dilated stenosis in an artery to prevent restenosis. The balloon angioplasty catheter 120 has the same components as described for the balloon angioplasty catheter 60 of FIGS. 7 and 8 namely an outer shaft 11, an inner shaft 12, a guide wire 30 in a guide wire lumen 19 and an annular passageway 17 through which fluid can be passed to inflate or deflate the angioplasty balloon 122 and a radiopaque marker band 124. The sheath 110 consists of a flexible cylinder 112 having longitudinal cutout slots 116 and plastic longitudinal strips 113 both enclosed by an elastic cylinder 114 into which is placed an elastic radioactive source 118 having an elastic radiopaque marker band 115P at its proximal end and an elastic radiopaque marker band 115D at it distal end. One or more holes 119 situated proximal to the elastic cylinder 114 can allow blood to enter which, when using a perfusion balloon angioplasty catheter that is well known in the art of interventional cardiology, can allow perfusion of tissue lying distal to the inflated balloon 122'. FIG. 12B shows that when the angioplasty balloon 122' is inflated, it enlarges the cutout slots 116', and dilates the radioactive source 118' and elastic cylinder 114', but the strips 113' merely move radially outward without any appreciable change in width. This system 100 would operate by first using the angioplasty balloon angioplasty catheter 120 to dilate a vessel of the human body, then deflate the angioplasty balloon 120, slide the sheath 110 over the angioplasty balloon 120 as shown in FIG. 11 and then reinflate the balloon 120 to push the radioactive source 118 against the vessel wall. The angioplasty balloon 122 would then be deflated, and the system 110 would be removed from the patient's body.

FIG. 13 shows a distal section of a sheath 130 which has an elastic shaft 136 onto which is mounted an elastic cylindrical radioactive source 134 having a proximal elastic radiopaque marker band 132P and a distal elastic radiopaque marker band 132D. This sheath 130 could be used in the same manner as the sheath 110 of FIG. 11.

All the embodiments described herein have a common feature of a radioactive source that is placed within an inflatable structure so as to place the radioactive source either against or in close proximity to an arterial wall at a site that is being or has been dilated. Except for the invention that has a radioactive material formed into the plastic material of an angioplasty balloon, all other embodiments of this invention utilize highly elastic material into which a radioactive material is placed in order to form a generally cylindrically shaped, elastic, radioactive source.

The plastic materials of the balloon angioplasty catheter (such as polyurethane, polyethylene, etc.) are well known in the art of interventional cardiology. The elastic material for the elastic balloon of the elastic balloon catheter would typically be an elastomer such as silicone or natural rubber. The elastic radiopaque marker bands could be formed from powdered tungsten placed into a low durometer silicone rubber. The radiopaque marker bands are typically formed from a high density metal such as tantalum. The wall thickness of a radioactive source or an elastic balloon prior to inflation would typically be 0.03 to 0.2 mm.

FIGS. 14 and 15 show a simplified design for a balloon angioplasty catheter with an angioplasty balloon and a cylindrical radioactive source. Specifically, FIGS. 14 and 15 show a balloon angioplasty catheter system 140 having an outer shaft 11, an inner shaft 12, a proximal radiopaque marker band 13P, a distal radiopaque marker band 13D, an annular passageway 17 that is used to inflate the angioplasty balloon 151, and a guide wire lumen 19 through which a guide wire 33 can move slideably. The balloon 151 is placed within an elastic cylindrical radioactive source 152 that has tapered distal and proximal ends 153. The cylinder 152 can be adhesively joined to the angioplasty balloon 151 along one narrow longitudinal line. This type of attachment is required so that the atherectomy balloon 151 can expand by unfolding its folds 154 (which unfolding is shown in FIGS. 10B and 12B) without tearing or distorting the elastic cylindrical radioactive source 152. The tapered ends 153 allow safer and easier advancement and retrieval of the balloon angioplasty catheter system 140 without causing the cylinder 152 to be pushed off the angioplasty balloon 151.

Figure 16:
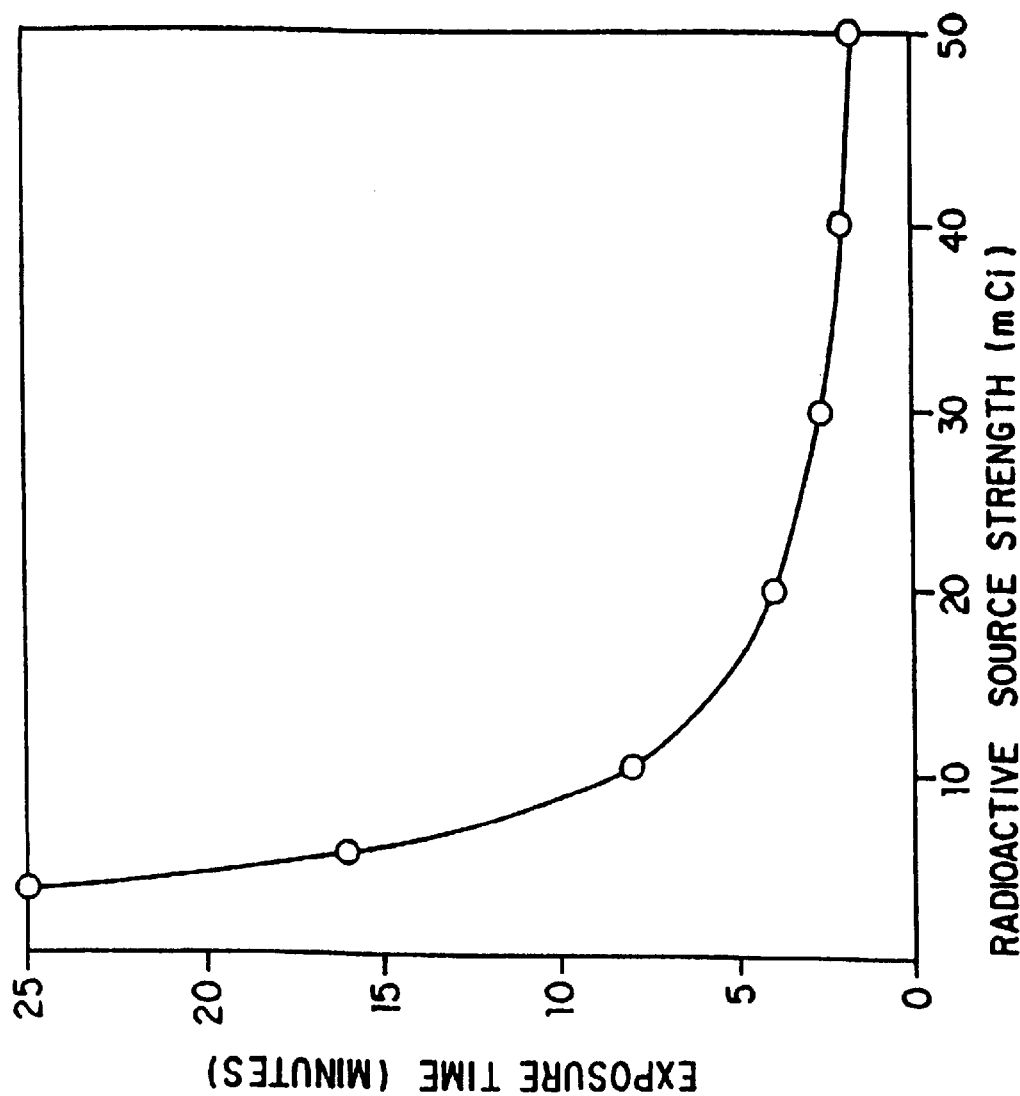
FIG. 16 illustrates the exposure time as a function of source strength for exposing a dilated arterial stenosis to irradiation for the purpose of decreasing restenosis.

Typical radiation exposure times for a patient using a 2.5 mm diameter balloon as a function of the source strength of P-32 for a cylindrical elastic radioactive source that is 2 cm long is shown in FIG. 16. The exposure time for a specific radioactive source strength should be increased proportionally to the length of the cylindrical radioactive source. Therefore, for a 4 cm long cylinder radioactive source, the P-32 source strength should be doubled. The exposure time for a specific radioactive source strength should also be increased as a function of increasing the inflated diameter of the radioactive source. This exposure time can be provided by a simple look-up table. It is highly desirable to limit the exposure time of the patient to be approximately the same time that it takes for pre-dilatation of an arterial stenosis. Ideally, the source strength of P-32 for a 2 cm long cylindrical radioactive source should be between 50 milliCuries (mCi) at the start of a 14 day nominal shelf life to 25 mCi at the end of the catheter's nominal shelf life. Since these are comparatively high levels of radioactivity, it is important to have a method for safe disposal of the radioactive sources after they are used. Since the cylindrical P-32 radioactive source has a half-life of 14.3 days, the radioactivity decreases by a factor of approximately 1,000 in 5 months. Therefore, if placed in a controlled space for 20 months, the radioactivity of a 50 mCi source would be down by 4 factors of 1,000, which is a factor of $10^{-12}$ so that the 50 mCi source would have an activity at 20 months of only $0.05 \times 10^{-6}$ microCuries. Such low levels of radiation (and even higher levels) are readily disposable into commercial trash systems. Therefore, the problem of disposing of used catheter systems is easily accomplished.

Any of the axially extending assemblies described herein is best used with a radiation shield that is located external to the patient's body as is described in U.S. patent application Ser. No. 08/408,780. Such a shield is essential to protect health care workers from being irradiated by the comparatively high intensity radioactive source located at a distal section of the catheters described herein.

It should also be understood that any of the radioactive elastic or angioplasty balloon assemblies described herein could be made in the form of a perfusion type balloon so as to allow continuous perfusion of the distal tissue during the irradiation procedure.

Another method for obtaining distal profusion is to utilize a hollow guide wire 33 as shown in FIGS. 14 and 15 through which an oxygenated fluid can be passed. The use of such a hollow guide wire 33 is described in U.S. Pat. No. 5,407,426 by J. R. Spears.

It should also be understood that a coating such as a lubricity coating could be applied to the exterior surface of an expandable radioactive source to prevent leaching out of a radioisotope contained within the elastic or plastic material of the radioactive source.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A balloon catheter system comprising a balloon catheter, an inflation liquid and a flexible guide wire, the balloon catheter having a distal section and also having an inflatable balloon and a generally cylindrical, thin-walled, elastic radioactive source both located coaxially at the distal section of the balloon catheter, the inflatable balloon being adapted to be inflated by injection into the balloon of the inflation liquid, the elastic radioactive source having a proximal end and a distal end and being adapted to move radially outward as a result of the injection of the inflation liquid into the inflatable balloon thus placing the radioactive source in close proximity to the wall of a vessel of the human body into which the balloon catheter has been inserted.

2. The balloon catheter system of claim 1 wherein the radioactive source is predominantly a beta particle emitter.

3. The balloon catheter system of claim 2 wherein the beta particle emitter is phosphorous-32.

4. The balloon catheter system of claim 2 wherein the beta particle emitter is yttrium-90.

5. The balloon catheter system of claim 1 wherein the inflatable balloon is an angioplasty balloon.

6. The balloon catheter system of claim 1 wherein the inflatable balloon is an elastic balloon.

7. The balloon catheter system of claim 1 wherein a first radiopaque marker band is used to indicate the proximal end of the elastic radioactive source and a second radiopaque marker band is used to indicate the distal end of the elastic radioactive source.

8. The balloon catheter system of claim 1 wherein the balloon catheter includes a guide wire lumen and the guide wire is an oxygenation guide wire that is adapted to perfuse tissue located distally to the inflatable balloon.

9. The balloon catheter system of claim 1 wherein the balloon catheter includes a guide wire lumen and the guide wire is placed through the guide wire lumen, the guide wire having a high density metal, highly radiopaque distal portion for indicating the longitudinal position of a dilated stenosis which is to be irradiated by the elastic radioactive source.

10. The balloon catheter system of claim 1 wherein the inflation liquid is a highly concentrated contrast medium having a concentration of at least 55% of an iodine based radiopaque liquid in normal saline solution.

11. The balloon catheter system of claim 10 wherein the inflation liquid includes a material having an atomic number greater than 53.

12. The balloon catheter system of claim 1 wherein the elastic radioactive source is made from silicone rubber into which a radioisotope has been placed.

13. The balloon catheter system of claim 12 wherein the radioisotope is a compound of phosphorous 32.

14. The balloon catheter system of claim 13 wherein the compound containing phosphorous 32 is adenosine triphosphate.

15. The balloon catheter system of claim 13 wherein the compound containing phosphorous 32 is orthophosphate.

16. The balloon catheter system of claim 1 wherein the balloon catheter has both an angioplasty balloon and an elastic balloon placed coaxially at the distal section of the balloon catheter.

17. The balloon catheter system of claim 16 wherein the elastic balloon is positionally located inside the angioplasty balloon.

18. The balloon catheter system of claim 16 wherein the elastic balloon is positionally located outside the angioplasty balloon.

19. The balloon catheter system of claim 16 wherein the elastic radioactive source is fixedly attached to the elastic balloon.

20. The balloon catheter system of claim 1 wherein the inflatable balloon of the balloon catheter is an angioplasty balloon and the elastic radioactive source is in the form of a cylinder that surrounds the angioplasty balloon.

21. The balloon catheter system of claim 20 wherein the elastic radioactive source is tapered at both its proximal end and its distal end.

22. A balloon angioplasty catheter having a distal section; an angioplasty balloon formed from a plastic material located at the distal section of the balloon angioplasty catheter, the angioplasty balloon having a radioactive material incorporated into the plastic material from which the angioplasty balloon is formed.

23. The balloon angioplasty catheter of claim 22 wherein the radioactive source is predominantly a beta particle emitter.

24. The balloon angioplasty catheter of claim 22 wherein the beta particle emitter is phosphorous-32.

25. An elastic balloon catheter having a distal section; an elastic balloon formed from an elastomer located at the distal section of the elastic balloon catheter and a radioactive material incorporated into the elastomer from which the elastic balloon is formed.

26. The elastic balloon catheter of claim 25 wherein the radioactive material is predominantly a beta particle emitter.

27. The elastic balloon catheter of claim 25 wherein the beta particle emitter is phosphous-32.

28. The elastic balloon catheter of claim 25 wherein the beta particle emitter is yttrium-90.

29. A system for dilating and irradiating an arterial stenosis the system comprising:
- a balloon angioplasty catheter having a distal section and having an angioplasty balloon located at the distal section of the balloon angioplasty catheter; and
- a sheath situated coaxially around the balloon angioplasty catheter and adapted to move slideably over the balloon angioplasty catheter, the sheath having a distal section where a radioactive source in the form of an elastic cylinder is located.

30. A system for irradiating a dilated arterial stenosis without unduly irradiating health care workers, the system being adapted for placement into an artery of a human body; the system comprising:
- a balloon catheter having a proximal section and a distal section and having an inflatable balloon and an expandable radioactive source both located at the distal section of the balloon catheter; and
- a radiation shield being coaxially situated at the proximal section of the balloon catheter, the entire radiation shield remaining exterior to the human body while the balloon catheter is advanced through the radiation shield and into a vessel of the human body so as to place the radioactive source at the site of the dilated arterial stenosis.

* * * * *